United States Patent [19]

Levy

[11] Patent Number: 5,020,995

[45] Date of Patent: Jun. 4, 1991

[54] SURGICAL TREATMENT METHOD AND INSTRUMENT

[76] Inventor: Guy Levy, 49, rue Croix de Regnier, F-13004 Marseille, France

[21] Appl. No.: 299,472

[22] Filed: Jan. 18, 1989

[51] Int. Cl.⁵ .............................................. A61C 5/00
[52] U.S. Cl. ................................... 433/215; 433/216; 606/15; 606/16
[58] Field of Search .................... 433/215, 216; 606/3, 606/10, 15, 16

[56] References Cited

U.S. PATENT DOCUMENTS

| | | | |
|---|---|---|---|
| 4,273,535 | 6/1981 | Yamamoto et al. | 433/216 |
| 4,503,853 | 3/1985 | Ota et al. | 433/215 |
| 4,521,194 | 6/1985 | Meyers et al. | 433/215 |
| 4,672,969 | 6/1987 | Dew | 606/3 |
| 4,784,135 | 11/1988 | Blum et al. | 128/303.1 |
| 4,818,230 | 4/1989 | Meyers et al. | 433/215 |
| 4,826,431 | 5/1989 | Fujimura et al. | 433/215 |
| 4,940,411 | 7/1990 | Vassiliadis et al. | 433/215 |

Primary Examiner—Cary E. Stone
Attorney, Agent, or Firm—Spensley, Horn, Jubas & Lubitz

[57] ABSTRACT

A method and apparatus for cutting tooth tissue by generating laser radiation at a wavelength which is absorbed more strongly by hydroxyapatite than by water; producing a succession of pulses of the generated radiation with an energy level, pulse duration, and repetition rate selected to cut the tooth tissue without causing harmful side effects; and concentrating the radiation pulses on the tissue to a spot sufficiently small to cause cutting of the tissue.

27 Claims, 1 Drawing Sheet

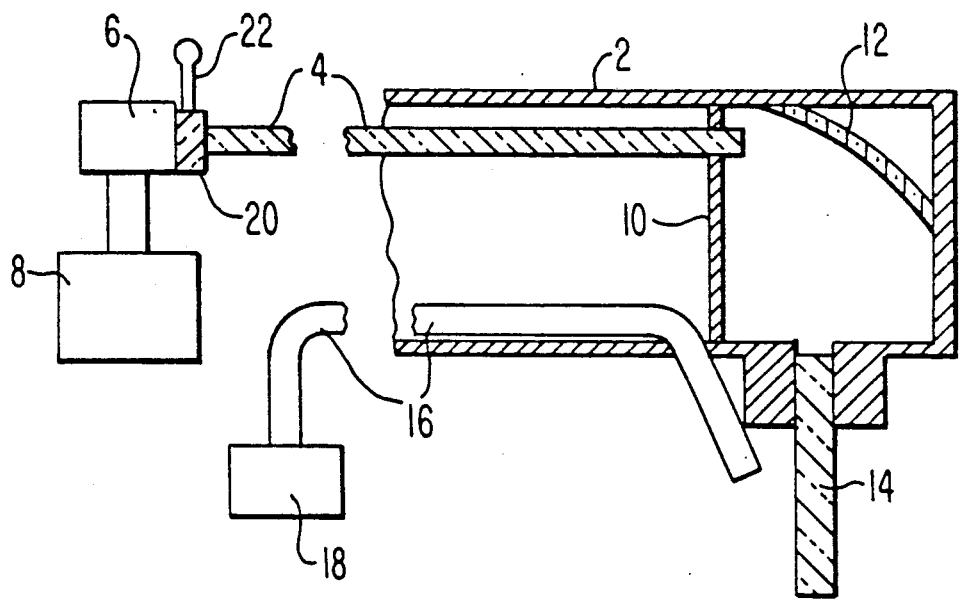

SURGICAL TREATMENT METHOD AND INSTRUMENT

BACKGROUND OF THE INVENTION

The present invention relates to surgical treatment procedures and instruments, and particularly utilizing laser radiation for the removal of tooth and gum tissue.

In dental procedures, it is frequently desirable to remove portions of tooth enamel and dentin, and in certain cases, portions of gum tissue, in an accurately controlled manner and there has been a growing interest in the use of laser radiation for performing such procedures. The use of laser radiation is attractive because, particularly with the aid of optical fibers, such radiation can be focused to a very small area and is thus compatible with the dimensional scale of dental procedures. Moreover, laser radiation procedures can be performed without recourse to an anesthetic.

While a number of devices of this type have been proposed, they have not proven to be of practical use notably because even the most effective of those devices already proposed are useful only under limited and very precisely defined conditions.

The enamel and dentin of a tooth include, as one component, hydroxyapatite, which is in amorphous form in the dentin and crystalline form in the enamel. These portions of a tooth additionally include organic tissues and water, but have no vascular system. Healthy dentin is in mineralized form, while dentin which has experienced decay is in demineralized form. Dentin has a relatively high percentage of organic tissue, around 40 percent, and also a high percentage of water. These percentages increase considerably in decayed dentin.

Tooth pulp and the gum surrounding the teeth consist of vascularized organic tissue containing both hemoglobin and water. Each of these components has a different response to laser radiation.

Thus, it has been found, that hydroxyapatite absorbs laser radiation in the wavelength ranges of 9–11 $\mu$, such as produced by $CO_2$ lasers, and also in the wavelength range 0.5–1.06 $\mu$, which includes the wavelength that can be produced by a YAG laser.

The laser radiation absorption by the various parts of a tooth at various wavelengths is influenced by the absorption of the radiation energy by the water component thereof. The greater the absorption by water, the less energy is available for absorption by the other components. Since the wavelengths of the radiation emitted by $CO_2$ lasers is absorbed to a large extent by water, this radiation has minimal cutting effect on enamel or dentin, and less of a cutting effect on mineralized dentin than on demineralized dentin.

On the other hand, it has been found that radiation at a wavelength of 1.06 $\mu$ is absorbed to a lesser degree by water, and therefore has a greater effect on mineralized tissues. Laser radiation at a wavelength of 0.532 $\mu$ is not absorbed at all by water and can be effective on mineralized tissues if a sufficiently high, and thus dangerous, power level is employed.

As regards vascularized tissues, radiation at the wavelengths emitted by $CO_2$ lasers has an effective cutting action because of its absorption by water, while radiation at a wavelength of 1.06 $\mu$ does not have any effect, and radiation at a wavelength of 0.532 $\mu$ has a cutting effect on soft tissues because, although not absorbed by water, it is well absorbed by hemoglobin.

While a particular wavelength may inherently have a cutting effect on enamel or dentin, it has been found that the practical utilization of radiation at such a wavelength for dental procedures is highly dependent on the form in which the radiation is applied, with respect to energy level, pulse duration and repetition rate. Specifically, efforts to apply such radiation in the form of high energy pulses of short duration have been found to produce a highly localized temperature increase, resulting in differential thermal expansion which can cause mechanical damage to the tooth as well as vascular damage to pulp tissue. Conversely, low energy pulses of long duration cause a more widespread heating of the tooth which results in patient discomfort as well as pulp damage due to heating.

SUMMARY OF THE INVENTION

It is an object of the present invention to effectively employ laser radiation in a variety of surgical operations involving cutting, by vaporization, of both tooth and gum tissue, as well as other vascularized body tissue.

Another object of the invention is to eliminate significant drawbacks of laser treatment systems which have previously been proposed.

A further object of the invention is to provide a single laser treatment device which can perform a variety of operations.

Yet another object of the invention is to perform dental treatments employing laser radiation in a manner to minimize or completely eliminate undesirable side effects of the treatment.

A specific object of the invention is to employ laser radiation to cut mineralized dental tissue without requiring high energy levels.

A further specific object of the invention is to employ laser radiation to cut soft tissue without requiring high energy levels.

BRIEF DESCRIPTION OF THE DRAWING

The sole Figure is a cross-sectional view of a preferred embodiment of an instrument for performing laser radiation treatments according to the invention.

DESCRIPTION OF THE PREFERRED EMBODIMENTS

The present invention is based essentially on the discovery that laser radiation can be used to cut, by vaporization, both tooth and gum material, as well as other vascularized tissue, with essentially no adverse side effects, if specific parameters are established for the laser radiation.

According to the present invention, the drawbacks described earlier herein can be eliminated, or at least substantially minimized, and an effective cutting action can be achieved, by the use of laser radiation preferably at a wavelength of 1.06 $\mu$ in the form of pulses having an energy content of between 10 and 50 mJ, with a pulse duration of the order of 100–300 microseconds, and a repetition rate of the order of 50 Hz, and with the radiation beam concentrated at a spot, at the treatment location, of the order of 200–600 $\mu$.

A pulse duration of 100–300 $\mu$ sec. has been found to be sufficiently long to avoid subjecting the tissue being treated to thermal shocks but sufficiently short to enable effective control of the heating action to be maintained.

According to the invention, laser radiation at a wavelength of 1.06 $\mu$, which can be produced by an Nd YAG laser, can be used for cutting, or vaporizing demineralized, i.e., decayed, enamel and dentin, without endangering gum tissue. Laser radiation at a wavelength of 0.532 μ which can also be produced by an Nd YAG laser, can also be used, but this requires great care because it has been found that radiation at this wavelength will also cut gum tissue. Therefore, radiation at this wavelength can be used when it is desired to cut gum tissue.

Further, applicant has discovered that laser radiation at the wavelength of 1.06 μ can be made to cut healthy, or mineralized, dentin, and healthy enamel, which was not heretofore considered possible, if a dark colored region is first provided at the spot where cutting is to begin. Specifically, it has been found that the absorption of energy at the wavelength of 1.06 nm by dark materials is sufficient to enable laser radiation having a suitable energy level to create a plasma which causes vaporization of dentin tissue. Applicant has further discovered that once a plasma cloud capable of vaporizing dentin has been established at a dark colored region, the laser beam can be displaced at a controlled speed from the dark colored region so that the plasma cloud will remain intact and vaporization of healthy dentin will continue.

For cutting dentin and enamel, laser radiation at a wavelength of 1.06 μ should be used. Radiation at a wavelength of 0.532 has been found to be effective only if applied at dangerously high energy levels.

Since radiation at 0.532 μ can efficiently cut vascularized tissue, it can be used for general surgical procedures. In this case, the radiation pulses should have an energy level of not greater than 10 mJ, with a pulse duration of 100-300 μ sec., and the radiation may be focussed to a spot 200-600 μ in diameter. A pulse repetition rate of the order of 50 Hz may be employed.

The Figure illustrates a handpiece for supplying laser radiation in a form suitable for performing the operations described above. A housing 2 is provided in the form normally utilized for handpieces, which housing would be configured in a manner known in the art for ease of manipulation. The interior of housing 2 is provided with an optical fiber 4 having an input end coupled to a source 6 of monochromatic light, such as an Nd YAG laser producing radiation at a wavelength of 1.06 μ. Light source 6 is connected to an operating power source 8 which supplies pulses sufficient to cause light source 6 to produce light pulses having the desired parameters.

The free end of fiber 4, in the vicinity of the free end of housing 2, is supported by a suitable support plate 10 to direct light radiation onto a curved mirror 12 which deflects the radiation onto the receiving end of a further optical fiber 14. Mirror 12 additionally performs a focusing action which can focus the radiation emerging from fiber 4 to a point within fiber 14, preferably in the vicinity of the outlet end thereof. This will help to assure that the light emerging from fiber 14 can be concentrated at a sufficiently small spot on the tooth to be treated. Fiber 14 preferably has a very small diameter, possibly of the order of 250 μ.

Housing 2 additionally contains a hollow tube 16 which is connected to a source 18 of water and/or air and which has an outlet end positioned to direct a stream of the fluid supplied by source 18 into the immediate vicinity of the tooth region to which laser radiation is being applied.

In accordance with a particular novel feature of the invention, a plate 20 which is capable of influencing the laser radiation so as to double its frequency is slidably mounted on source 6 and is connected to a control handle 22 so as to be slidable, by manipulation of handle 22, between the illustrated position, where plate 20 is interposed in the light path between source 6 and fiber 4, and a retracted position, where plate 20 does not intersect the light path. With this simple arrangement, the handpiece is given the capability of applying either 1.06 μ or 0.532 μ radiation to the area to be treated, so that only a single laser device need be provided for the selective performance of procedures with radiation of either wavelength.

For performing endodontic treatments within a tooth canal, fiber 14 can be given a suitable length and diameter to be introduced into a canal in order to apply the radiation to the canal walls for widening the canal preparatory to filling.

According to a particular aspect of the invention, the requisite dark spot can be formed simply by applying a small amount of graphite, such as used in pencils, with the aid of a small amount of glue. In fact, it has been found possible to achieve the desired result by applying a small quantity of glue to the point of a sharpened pencil and then rubbing the pencil point at the desired location.

For removal of decay, the radiation can have a wavelength of 1.06 μ and be in the pulsed form described above.

To dissipate the heat generated by the radiation, water and/or air should be sprayed onto the tooth in the vicinity of the spot which is being irradiated. The rate of flow of fluid depends on the extent to which the fluid absorbs the radiation. For example, water absorbs radiation at 1.06 nm at a very low level, but higher than radiation at 0.532 nm. Therefore, water would be delivered at a higher rate when the latter radiation wavelength is being employed.

When the radiation is applied to demineralized enamel or pathological dentin, a dark spot is not necessary and a plasma forms at the irradiation spot and the affected material is volatilized at and around the spot. The extent of the plasma tends to increase in a short time and this allows for the possibility of reducing the pulse energy to between 10 and 20 mJ.

When cutting normal tissue, the radiation wavelength can be 1.06 μ, which requires application of a dark spot, and will not affect soft tissues, or 0.532 μ, which can cut either hard tissues, i.e., dentin and enamel, or soft, vascularized tissues. Each wavelength will be preferable for certain purposes.

Thus, the invention provides four operating modes responsive to different needs:

1) For cutting demineralized enamel and pathological dentin, use is made of radiation at a wavelength of 1.06 μ, an energy level of 20-50 mJ, and with the pulse parameters described earlier herein. Labelling with a dark spot is not required.

2) For cutting normal enamel and dentin, the radiation would have the same parameters as for mode 1), but the starting point would be labelled with a dark spot.

3) For cutting any tissue, the same parameters as for mode 1) would be employed, with labelling with a dark spot where possible.

4) For cutting vascularized tissue, including gum and other soft body tissue, laser radiation at a wavelength of 0.532 μ would be used, composed of pulses having an energy level of no greater than 10 mJ, without requiring labelling with a dark spot.

For dental treatments, a cooling spray will be used whenever the operation generates a sufficient level of heat.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for cutting tooth tissue comprising: imparting a dark coloration to the tooth tissue at a location where the tissue is to be cut; generating laser radiation at a wavelength which is absorbed more strongly by hydroxyapatite than by water; producing a succession of pulses of the generated radiation with an energy level, pulse duration, and repetition rate selected to cut the tooth tissue without causing harmful side effects; and concentrating the radiation pulses on the tissue at the location of the dark coloration and to a spot sufficiently small to cause cutting of the tissue.

2. A method as defined in claim 1 wherein the wavelength of the radiation is 1.06 $\mu$.

3. A method as defined in claim 1 wherein each pulse applied to the tissue has an energy content of between about 10 and 50 mJ.

4. A method as defined in claim 3 wherein each pulse applied to the tissue has an energy content of between about 20 and 50 mJ.

5. A method as defined in claim 1 wherein said step of concentrating is carried out to limit the radiation to a spot having a diameter not exceeding about 250 $\mu$.

6. A method as defined in claim 5 wherein the spot has a diameter of between about 200 and 600 $\mu$.

7. A method as defined in claim 1 wherein the pulses have a repetition rate of the order of 50 Hz.

8. A method as defined in claim 1 wherein the pulses have a duration of about 100-300 $\mu$ sec.

9. A method as defined in claim 1 wherein the tooth tissue to be cut is healthy dentin.

10. A method as defined in claim 9 wherein said step of imparting comprises applying a black substance to the dentin.

11. A method as defined in claim 9 wherein the wavelength of the radiation is 1.06 $\mu$.

12. A method as defined in claim 1 further comprising supplying a cooling fluid to the region of the spot simultaneously with said concentrating step.

13. A method as defined in claim 12 wherein the fluid is water.

14. Apparatus for cutting tooth tissue comprising: means including an Nd YAG laser for generating laser radiation at a wavelength which is absorbed more strongly by hydroxyapatite than by water; means connected to said generating means for causing said generating means to produce a succession of pulses of the generated radiation with an energy level, pulse duration, and repetition rate selected to cut the tooth tissue without causing harmful side effects; and an exposed optical fiber disposed for concentrating the radiation on the tissue to a spot sufficiently small to cause cutting of the tissue said optical fiber having a diameter sufficiently small and a length sufficient to permit insertion of said fiber into a tooth canal.

15. Apparatus as defined in claim 14 wherein the wavelength of the radiation is between 0.5 and 1.1 $\mu$.

16. Apparatus as defined in claim 15 wherein the wavelength of the radiation is about 0.532 and $\mu$.

17. Apparatus as defined in claim 15 wherein the wavelength of the radiation is about 106 $\mu$.

18. Apparatus as defined in claim 14 further comprising means disposed for supplying a cooling fluid to the region of the spot simultaneously with application of the radiation.

19. A method for cutting vascularized tissue comprising:
generating radiation by means of an Nd YAG laser;
acting on the radiation produced by the laser in a manner to double its frequency;
producing a succession of pulses of the frequency doubled radiation with an energy level, pulse duration and repetition rate selected to cut the tissue without causing harmful side effects; and
concentrating the radiation pulses on the tissue to a spot sufficiently small to cause cutting of the tissue.

20. A method as defined in claim 19 wherein each pulse applied to the tissue has an energy content of not greater than about 10 mJ.

21. A method for cutting tooth tissue comprising generating radiation by means of a NdYAG Laser; producing a succession of pulses of the generated radiation with an energy level, pulse duration, and repetition rate selected to cut the tooth tissue without causing harmful side effects; concentrating the radiation pulses on the tissue to a spot sufficiently small to cause cutting of the tissue; and supplying a cooling fluid to the tissue at the location of application of the radiation pulses.

22. A method for cutting tooth dentin comprising: generating laser radiation at a wavelength which is absorbed more strongly by hydroxyapatite than by water; producing a succession of pulses of the generated radiation with an energy level, pulse duration, and repetition rate selected to cut tooth dentin without causing harmful side effects; and concentrating the radiation pulses on tooth dentin to a spot sufficiently small to cause cutting of the dentin.

23. A method as defined in 22 further comprising: supplying a cooling fluid to the dentin at the location of application of the radiation pulses.

24. A method as defined in claim 23 where the cooling fluid is water.

25. A method as defined in claim 22, further comprising imparting a dark coloration to the dentin at the location where the dentin is to be cut prior to said step of concentrating the radiation pulses.

26. A method as defined in claim 22 wherein the laser radiation is generated by an Nd:YAG laser.

27. A method for removing tissue from the walls of a tooth canal comprising:
generating laser radiation at a wavelength which is absorbed more strongly by hydroxyapatite than by water, the laser radiation being in the form of a succession of pulses with an energy level, pulse duration and repetition rate selected to cut the tissue; introducing an optical fibre into the tooth canal;
and delivering the laser radiation to the wall of the tooth canal via the optical fibre.

* * * * *

UNITED STATES PATENT AND TRADEMARK OFFICE
CERTIFICATE OF CORRECTION

PATENT NO. : 5,020,995
DATED : June 4, 1991
INVENTOR(S) : Guy Levy

It is certified that error appears in the above-identified patent and that said Letters Patent is hereby corrected as shown below:

Column 6, line 8, delete "and";

Column 6, line 10, change "106" to -- 1.06 --.

Signed and Sealed this

Twenty-fifth Day of May, 1993

Attest:

MICHAEL K. KIRK

*Attesting Officer*  *Acting Commissioner of Patents and Trademarks*